United States Patent
Fojtik

(10) Patent No.: US 10,335,133 B2
(45) Date of Patent: Jul. 2, 2019

(54) EXPANDABLE DEVICES FOR POSITIONING ORGANS

(71) Applicant: Manual Surgical Sciences, LLC, Boulder, CO (US)

(72) Inventor: Shawn P. Fojtik, Park City, UT (US)

(73) Assignee: Manual Surgical Sciences L.L.C., Minneapolis, MN (US)

(*) Notice: Subject to any disclaimer, the term of this patent is extended or adjusted under 35 U.S.C. 154(b) by 168 days.

(21) Appl. No.: 14/635,435

(22) Filed: Mar. 2, 2015

(65) Prior Publication Data
US 2015/0245829 A1 Sep. 3, 2015

Related U.S. Application Data

(60) Provisional application No. 61/946,392, filed on Feb. 28, 2014.

(51) Int. Cl.
| | | |
|---|---|---|
| *A61B 17/02* | (2006.01) | |
| *A61M 25/00* | (2006.01) | |
| *A61B 90/00* | (2016.01) | |
| *A61B 17/00* | (2006.01) | |
| *A61B 17/22* | (2006.01) | |

(52) U.S. Cl.
CPC .......... *A61B 17/0218* (2013.01); *A61B 90/04* (2016.02); *A61M 25/00* (2013.01); *A61M 25/0082* (2013.01); *A61B 2017/00557* (2013.01); *A61B 2017/22071* (2013.01); *A61B 2090/0427* (2016.02); *A61B 2090/3966* (2016.02); *A61M 2025/0096* (2013.01)

(58) Field of Classification Search
CPC .............. A61M 29/02; A61M 25/1002; A61M 25/1011; A61M 25/1018
See application file for complete search history.

(56) References Cited

U.S. PATENT DOCUMENTS

| | | |
|---|---|---|
| 5,531,776 A | 7/1996 | Ward et al. |
| 5,558,665 A | 9/1996 | Kieturakis |
| 6,067,990 A | 5/2000 | Kieturakis |
| 6,371,910 B1 | 4/2002 | Zwart et al. |

(Continued)

FOREIGN PATENT DOCUMENTS

WO WO2012148966 * 11/2012 ............. A61B 18/02

OTHER PUBLICATIONS

United States Patent and Trademark Office Acting as the International Searching Authority, "International Search Report and Written Opinion," dated May 27, 2015, in international application No. PCT/US2015/018283.

(Continued)

*Primary Examiner* — Carrie R Dorna
(74) *Attorney, Agent, or Firm* — Durham Jones & Pinegar, P.C., Intellectual Property Law Group

(57) ABSTRACT

A positioning device is configured to selectively position or otherwise manipulate one or more organs within the body of a subject. The positioning device includes a shaped expandable element that is configured to be selectively transitioned between an unexpanded, or collapsed, state and an expanded state. While in the expanded state, the expandable element repositions or otherwise manipulates an organ. Systems that include positioning devices are also disclosed, as are methods for positioning or otherwise manipulating organs.

15 Claims, 4 Drawing Sheets

(56) References Cited

U.S. PATENT DOCUMENTS

| | | | |
|---|---|---|---|
| 6,632,235 B2* | 10/2003 | Weikel | A61B 17/025 606/192 |
| 6,746,465 B2 | 6/2004 | Diederich et al. | |
| 7,476,235 B2 | 1/2009 | Diederich et al. | |
| 7,621,908 B2 | 11/2009 | Miller | |
| 7,819,817 B2 | 10/2010 | Rahn | |
| 8,273,016 B2 | 9/2012 | O'Sullivan | |
| 8,454,588 B2 | 6/2013 | Rieker et al. | |
| 8,506,589 B2 | 8/2013 | Maloney | |
| 8,529,443 B2 | 9/2013 | Maloney | |
| 9,173,705 B2 | 11/2015 | Whayne et al. | |
| 2007/0118097 A1 | 5/2007 | Miller | |
| 2007/0299433 A1* | 12/2007 | Williams | A61B 18/02 606/21 |
| 2008/0033415 A1 | 2/2008 | Rieker et al. | |
| 2009/0112248 A1* | 4/2009 | Maloney | A61B 18/1492 606/191 |
| 2011/0082488 A1* | 4/2011 | Niazi | A61M 25/1002 606/192 |
| 2011/0282338 A1 | 11/2011 | Fojtik | |
| 2014/0094839 A1* | 4/2014 | Nimkar | A61M 25/0102 606/191 |
| 2015/0196743 A1 | 7/2015 | Diederich et al. | |

OTHER PUBLICATIONS

European Patent Office, Extended Search Report in European Patent Application No. 15754623.5, dated Sep. 29, 2017.
Japanese Patent Office, Notice of Reasons for Rejection in Japanese Patent Application No. 2016-554609, dated Oct. 18, 2017.
Japanese Patent Office, Notice of Allowance in Japanese Patent Application No. 2016-554609, dated Aug. 17, 2018.
Japanese Patent Office, Certificate of Patent 6389267 from Japanese Patent Application No. 2016-554609, dated Aug. 24, 2018.

* cited by examiner

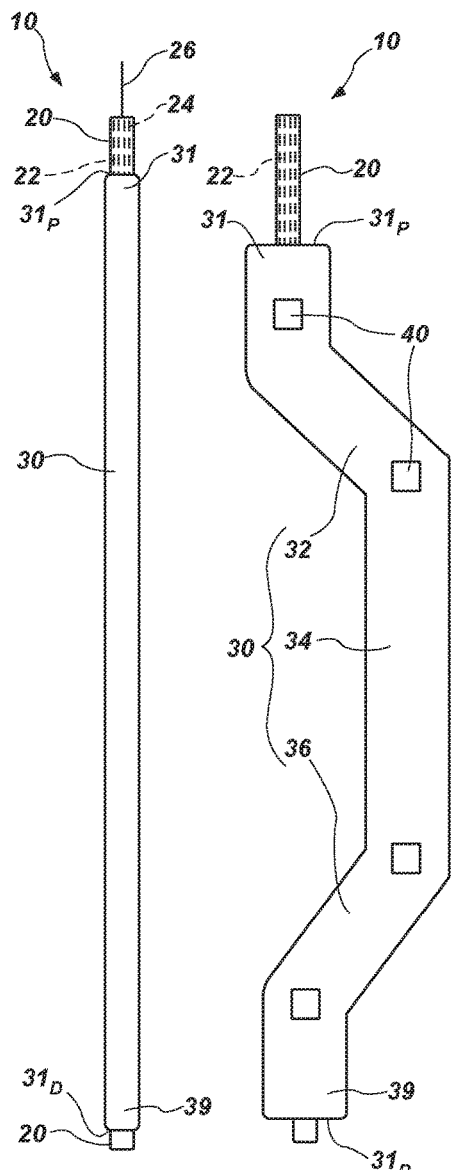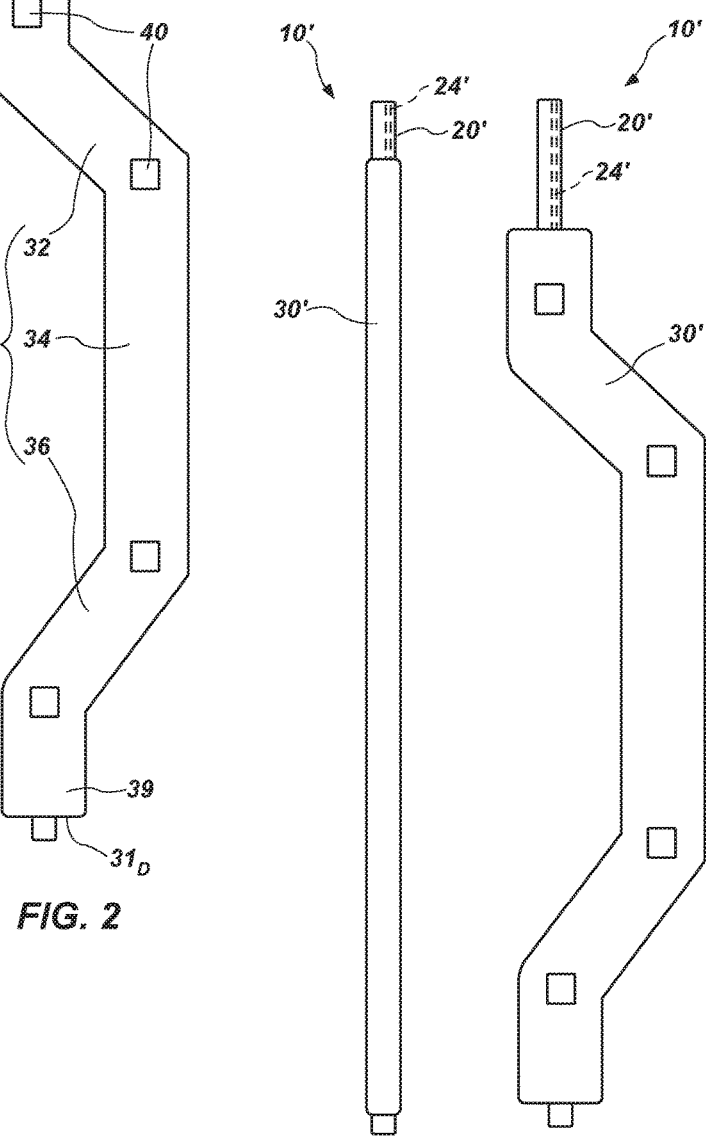

EXPANDABLE DEVICES FOR POSITIONING ORGANS

CROSS-REFERENCE TO RELATED APPLICATION

A claim for the benefit of priority to the Feb. 28, 2014 filing date of U.S. Provisional Patent Application No. 61/946,392, titled EXPANDABLE DEVICES FOR POSITIONING ORGANS ("the '392 Provisional Application"), is hereby made pursuant to 35 U.S.C. § 119(e). The entire disclosure of the '392 Provisional Application is hereby incorporated herein.

TECHNICAL FIELD

This disclosure relates generally to devices for selectively positioning or otherwise manipulating organs (e.g., hollow organs, organs adjacent to internal body cavities, etc.) within the body of a subject. A positioning device according to this disclosure may include an expandable element with a shape that will position a hollow organ, such as an esophagus, in a desired manner. Systems that include organ positioning devices are also disclosed, as are methods for positioning organs.

SUMMARY

A positioning device according to this disclosure may be configured for introduction into a hollow organ or an internal body cavity and against a surface of an organ. The positioning device may include a shaft and an expandable element. The shaft may have a longitudinal axis, which may be the longitudinal axis of the positioning device. The shaft may be configured to enable introduction of the positioning device and, more specifically, its expandable element, into the body of a subject and into a hollow organ that is to be repositioned or otherwise manipulated. Alternatively, the shaft may be introduced into an internal cavity within a subject's body adjacent to at least one organ that is to be repositioned or otherwise manipulated.

The expandable element is positioned along a length of the shaft. It may be located at an intermediate position along a length of the shaft, with portions of the shaft located proximal to and distal to the expandable element. Alternatively, the expandable element may be located at a distal end of the shaft.

The expandable element may have an unexpanded state and an expanded state. The unexpanded state, or collapsed state, of the expandable element may facilitate its introduction into a subject's body and into the hollow organ or internal cavity, as well as its removal from the hollow organ or internal cavity and the body. While in the unexpanded state, the expandable element may be flaccid or substantially flaccid and, thus, easily manipulated (e.g., bent, otherwise conform to a desired shape, etc.).

The expanded state of the expandable element may enable it to assume a desired shape, which may provide the positioning device with an asymmetrical structure. In some embodiments, the expandable element may include a divergent section, a spacing section and, optionally, a convergent section. The divergent section of the expandable element may at least partially diverge from the longitudinal axes of the shaft and the positioning device while in the expanded state. The spacing section of the expandable element, which is distal to the divergent section, may be configured to move, stretch or otherwise manipulate the tissues of a hollow organ in which the expandable element is disposed or an organ against which the expandable element is positioned and, thus, to modify the position and/or shape of the organ. In embodiments where the positioning device includes a convergent section, the convergent section may reinforce the new position and/or shape of a portion of the hollow organ in which the expandable section resides or against which the expandable section has been positioned, as defined at least in part by the spacing section. The abilities of the divergent section, the spacing section and any optional convergent section to move, reshape or otherwise manipulate an organ or a portion thereof may, in some embodiments, result from a substantial rigidity (e.g., the rigidity provided by a gas inflated (e.g., to a pressure of about 8 atm. to about 15 atm., etc.) or fluid inflated element, etc.) or a rigidity of the expandable element while in its expanded state.

In use, the expandable element of a positioning device, while in its unexpanded state, may be introduced into the body of a subject, and into an interior of a hollow organ or into an internal cavity of the body. In some embodiments, the expandable element may be placed at a particular location and in a particular orientation within the hollow organ or internal cavity. Once the expandable element is in place within the hollow organ or internal cavity, it may be expanded. Expansion of the expandable element may move, stretch or otherwise manipulate some or all of the hollow organ or internal cavity. With an organ moved or otherwise manipulated in a desired manner, other procedures may be performed. After those procedures are complete, the expandable element may be returned to its unexpanded state, which may reverse movement other manipulation of part or all of the organ. The expandable element may then be removed from the hollow organ or internal cavity, and the expandable element and the positioning device may be removed from the body of the subject.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 1 illustrates an embodiment of a positioning device, which includes a shaft and an expandable element positioned over an intermediate portion of the shaft, with the expandable element in an unexpanded state;

FIG. 2 illustrates the embodiment of positioning device shown in FIG. 1, with the expandable element in an expanded state;

FIG. 3 depicts another embodiment of positioning device, which includes a shaft and an expandable element positioned over a distal portion of the shaft, with the expandable element in an unexpanded state;

FIG. 4 depicts the embodiment of positioning device shown in FIG. 3, with the expandable element in an expanded state;

DETAILED DESCRIPTION

Figures 5, 6:
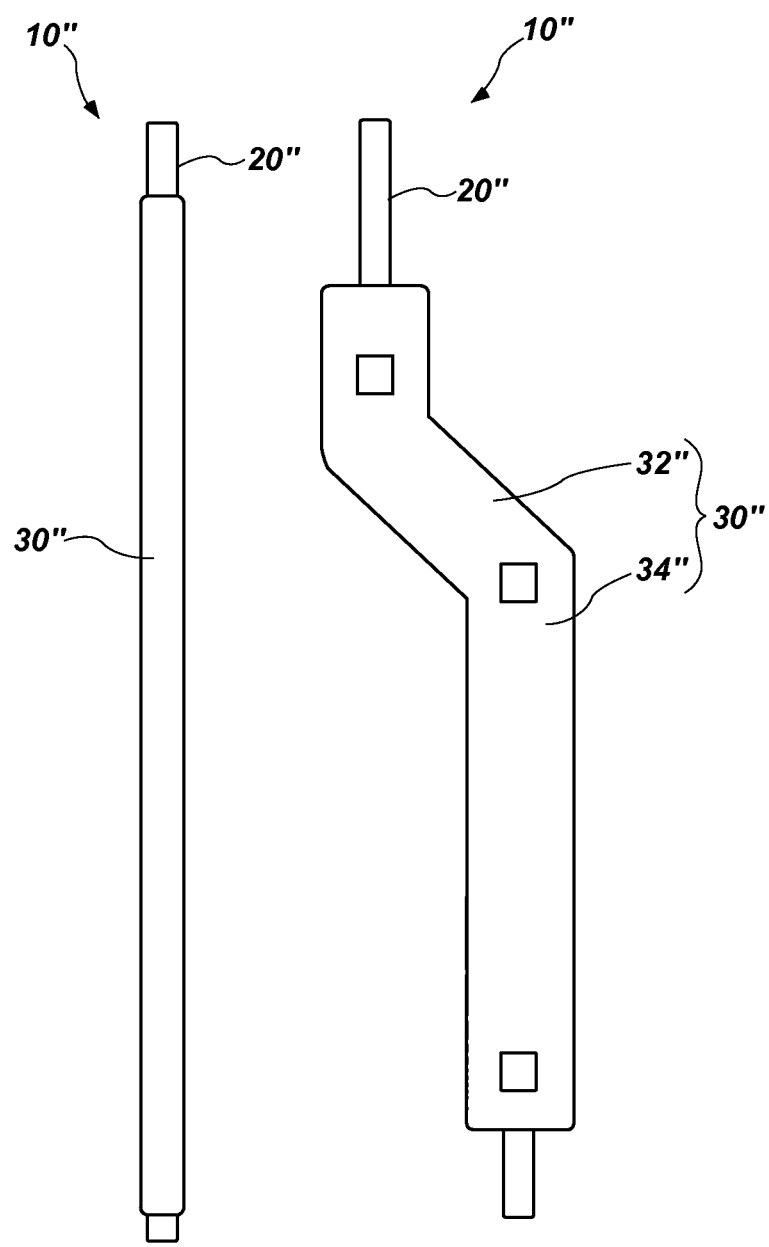
FIG. 5 shows yet another embodiment of positioning device, which includes a shaft and another embodiment of expandable element on the shaft, with the expandable element in an unexpanded state.
FIG. 6 shows the embodiment of positioning device depicted by FIG. 5, with the expandable element in an unexpanded state.

With reference to FIGS. 1 and 2, an embodiment of a positioning device 10 that incorporates teachings of this disclosure is illustrated. The positioning device 10, which is configured to move and/or manipulate a portion of a hollow organ within which it is positioned, includes a shaft 20 and an expandable element 30.

The shaft 20 of the positioning device 10 comprises an elongated element, and may include a longitudinal axis, which may define a longitudinal axis of the positioning device 10. The shaft 20 is configured to enable introduction of the expandable element 30 into the body of a subject, and placement of the expandable element 30 at a desired location and in a desired orientation within the body; for example, within a hollow organ in the body. The shaft 20 may have sufficient flexibility to enable its movement along curved, even tortious, paths through the body of a subject, to enable it to conform to the shape(s) of structures (e.g., organs, etc.) within which or against which it is positioned and/or to enable it to at least partially conform to the shape of the expandable element 30.

Without limitation, the shaft 20 may comprise a catheter. More specifically, the shaft 20 may comprise an over-the-wire (OTW) catheter, which may be configured to be placed over and introduced into the subject's body along a guide wire. Even more specifically, the shaft 20 may comprise a 6 French (F) to 9 F catheter that is configured for introduction on a 60 PPI to 90 PPI large braid guide wire with an outer diameter of up to about 0.038 inch.

The shaft 20 may be configured to enable remote expansion and retraction of the expandable element 30. In embodiments where the shaft 20 comprises a catheter, the shaft 20 may include a lumen that enables an inflation medium, such as a gas or mixture of gases, air or a liquid, to be introduced into the expandable element 30 and/or withdrawn from the expandable element 30. In other embodiments, the shaft 20 may be configured to accommodate one or more elements (e.g., a control wire, etc.) that enable mechanical expansion and/or retraction of the expandable element 30.

As illustrated by FIGS. 1 and 2, respectively, the expandable element 30 of the positioning device 10 has an unexpanded state and an expanded state. In its unexpanded state, which is depicted by FIG. 1, the expandable element 30 may reside on an outer surface 22 of the shaft 20 with extending substantially beyond the outer surface 22. As shown in FIG. 2, in its expanded state, the expandable element 30 may extend beyond the outer surface 22 of the shaft 20. In addition, when the expandable element 30 expands, it may diverge from the longitudinal axes L of the shaft 20 and the positioning device 10.

In the embodiment depicted by FIGS. 1 and 2, the expandable element 30 includes, from its proximal side 31 to its distal side 39, a divergent section 32, a spacing section 34 and a convergent section 36. The divergent section 32 may be configured to move a portion of a hollow organ within which the divergent section 32 resides out of its normal location or, in the case of an elongated organ (e.g., an esophagus, a large intestine, a urethra, etc.), out of the normal path of the elongated organ. The spacing section 34, which is distal to the divergent section 32, is configured to hold a portion of an organ within which it resides in a particular position and/or in a particular shape. The convergent section 36, which is adjacent to the distal side of the spacing section 34, may be configured to hold the distal side of the spacing section 34 in place. Optionally, the convergent section 36 may be configured to accommodate organs or other structures within the body of a subject.

Various transitions, or bends, between differently oriented sections of the expandable element 30 (e.g., the transition between the divergent section 32 and the spacing section 34, the transition between the spacing section 34 and the convergent section 36, etc.) may be smooth. The smoothness of one or more transitions may be configured to reduce or eliminate the likelihood of trauma (i.e., a transition may be atraumatic) during and after placement of the expandable element 30 in its expanded state. In some embodiments, a transition, or bend, may comprise a curve. In other embodiments, a transition, or bend, may include outer corners that are radiused.

In a specific embodiment, in which the positioning device 10 and its expandable element 30 are configured for insertion into and manipulation of a human esophagus, the expandable element 30 may have a length of about 14 cm to about 16 cm, with the spacing section 34, which is located centrally along a length of the expandable element 30, being about 10 cm long. The divergent section 32 and the convergent section 36 may be configured to move the spacing section 34 laterally (in the orientation depicted by FIGS. 1 and 2) to a location that is substantially parallel to the longitudinal axis of the shaft 20, but with a longitudinal axis of the spacing section 34 being offset by about 15 mm from the longitudinal axis of the shaft 20. Upon placing the expandable element 30 in its expanded state, it may have an outer diameter of about 8 mm to about 12 mm.

The expandable element 30 may, in some embodiments, include one or more radiopaque features 40, which may enable a clinician to determine the position and, optionally, the orientation of the expandable element 30 within a hollow organ of a subject's body. In other embodiments, the expandable element 30 may comprise a radiopaque material (e.g., in embodiments where the expandable element 30 comprises a mesh, etc.).

As suggested previously herein, the expandable element 30 may be configured to be inflated with an inflation medium, such as a gas or mixture of gases, air or a liquid. An expandable element 30 that is configured for inflation may include ends 31P and 31D that are sealed against the shaft 20. The shaft 20 of a positioning device 10 with an expandable element 30 may include an inflation/deflation lumen 24 that communicates with an interior of the expandable element 30 and, thus, introduces an inflation medium into the expandable element 30 and removes the inflation medium from the expandable element 30 by way of one or more apertures (not shown) that extend through a wall of the shaft 20, from the inflation/deflation lumen 24 of the shaft 20 to an exterior of the shaft 20.

An expandable element 30 may be shaped in a desired manner, such as that depicted by FIGS. 1 and 2. Cross sectionally, the expandable element 30 may be circular, elliptical, have a tear shape, or have any other shape that will cause little or no trauma during and following expansion of the expandable element 30. Accordingly, the expandable element 30 may be formed from a material that can be shaped as desired. Without limitation, the material of an inflatable expandable element 30 may be moldable, capable of being welded with heat or ultrasonically, or otherwise formed into a desired shape. In addition, the material from which the expandable element 30 is formed may be compliant, semi compliant or substantially non compliant when the expandable element 30 is in its expanded state. Examples of suitable materials for use as the expandable element 30 include, but are not limited to, polyethylene, polyethylene terephthalate, and polyurethane.

As indicated previously herein, suitable media for expanding inflatable embodiments of expandable elements 30 include gases, gas mixtures, and air. Alternatively, the medium that is used to inflate an inflatable expandable element 30 may comprise a saline solution. In some embodiments, the saline solution may include a radio-opaque material, such as barium or a barium salt.

As an alternative to inflatable expandable elements 30, an expandable element 30 may be formed from a shaped mesh that surrounds at least a portion of the shaft 20. Without limitation, a shaped mesh may be formed from stainless steel, nitinol or any other suitable material. The mesh may be formed (e.g., annealed, etc.) to substantially conform to the shape and dimensions of the shaft 20, to enable the expandable element 30 to reside on the shaft 20 when the expandable element 30 is in its unexpanded state. The mesh may also be formed to impart the expandable element 30 with a predetermined shape and dimensions when put in its expanded state.

An expandable element 30 that is formed from or otherwise includes a shaped mesh may be mechanically expanded by any suitable, known means for expansion, such as one or more elements that introduce tension into the shaped mesh to cause it to expand, and that enable the shaped mesh to collapse when the tension is released, or relaxed. As a non-limiting example, an expandable element 30 may include one or more control wires 26 that are configured to mechanically expand and collapse the expandable element 30. Each control wire 26 may comprise a somewhat rigid element that may extend through an inflation/deflation lumen 24 of the shaft 20, and may be actuated (i.e., pulled and/or pushed) from a location at or near a proximal end of the shaft 20. As the positioning device 10 is being introduced into the body of a subject, each control wire 26 may be pushed forward to a position that maintains the expandable element 30 in its unexpanded state around and close to the shaft 20. When the expandable element 30 is at an appropriate location within a hollow organ, one or more control wires 26 may be pulled to expand one or more sections of the expandable element 30 a desired extent. Once use of the positioning device 10 is no longer needed (e.g., when deflection or other reshaping of the hollow organ is no longer needed, etc.), each control wire 26 may be pushed, which will cause the expandable element 30 to collapse to its unexpanded state, thereby facilitating removal of the expandable element 30 and the remainder of the positioning device 10 from the hollow organ.

Some embodiments of expandable elements 30 may include individually, or separately, inflatable sections (e.g., divergent section 32, spacing section 34, convergent section 36, etc., may be configured to be inflated and deflated independently from one another). In embodiments where the sections 32, 34, 36 of the expandable element 30 are individually inflatable, each section 32, 34, 36 may communicate with a separate inflation/deflation lumen 24 of a catheter that forms at least a part of the shaft 20 and through which inflation and/or deflation of a section 32, 34, 36 of the expandable element 30 may occur. In other embodiments, the sections 32, 34, 36 may be individually expandable and/or retractable by dedicated actuators (e.g., pull wires, etc.).

Expandable elements 30 with separately expandable sections 32, 34, 36 may enable a clinician to selectively expand the expandable element 30 in two or more sequences. As an example, and with continued reference to FIGS. 1 and 2, the spacing section 34 may be expanded first, causing the spacing section 34 to occupy space within the hollow organ. After the spacing section 34 has been at least partially expanded, one or both of the divergent section 32 and the convergent section 36 may be expanded to move the spacing section 34 and the portion of the hollow organ within which the spacing section 34 resides. Such a configuration may provide for increased control over the manner in which a portion of a hollow organ or an entire hollow organ is manipulated, including, without limitation, the distance the hollow organ is diverted or otherwise moved from its original location.

Turning now to FIGS. 3 and 4, an embodiment of positioning device 10' is illustrated that includes an expandable element 30' that resembles the embodiment of expandable element 30 shown in FIGS. 1 and 2. A shaft 20' of the positioning device 10' is, however, configured to be introduced into a body of a subject, or into a hollow organ within a body of a subject, without the need for a guide wire. Accordingly, the shaft 20' may lack an inflation/deflation lumen 24 (FIGS. 1 and 2) that accommodates a guide wire. The shaft 20' may, however, include one or more lumens 24' that enable expansion and/or contraction of the expandable element 30'. Without limitation, the shaft 20' of the positioning device 10' may include one or more lumens 24' for inflating/deflating the expandable element 30' or sections thereof, one or more lumens 24' for accommodating control wires 26 or one or more lumens 24' for accommodating other elements for expanding and contracting the expandable element 30 or sections thereof.

Referring now to FIGS. 5 and 6, yet another embodiment of positioning device 10" is shown. The positioning device 10" includes an embodiment of an expandable element 30" that comprises a divergent section 32" and a spacing section 34", but lacks a convergent section 36 (FIGS. 1 and 2).

Figure 8:
FIGS. 7 through 9 are radiographic images of use of an embodiment of positioning device according to this disclosure in a human esophagus.
Figure 7:
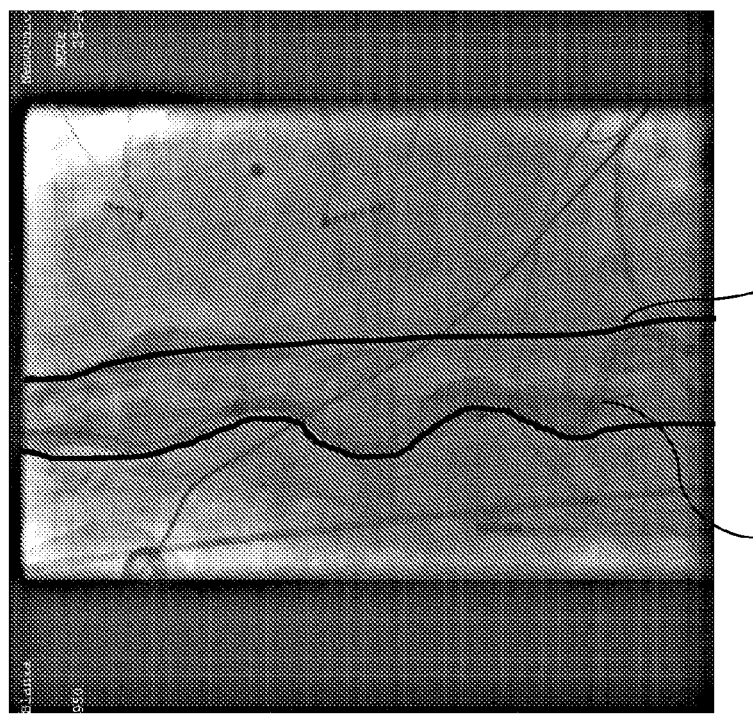
Figure 9:
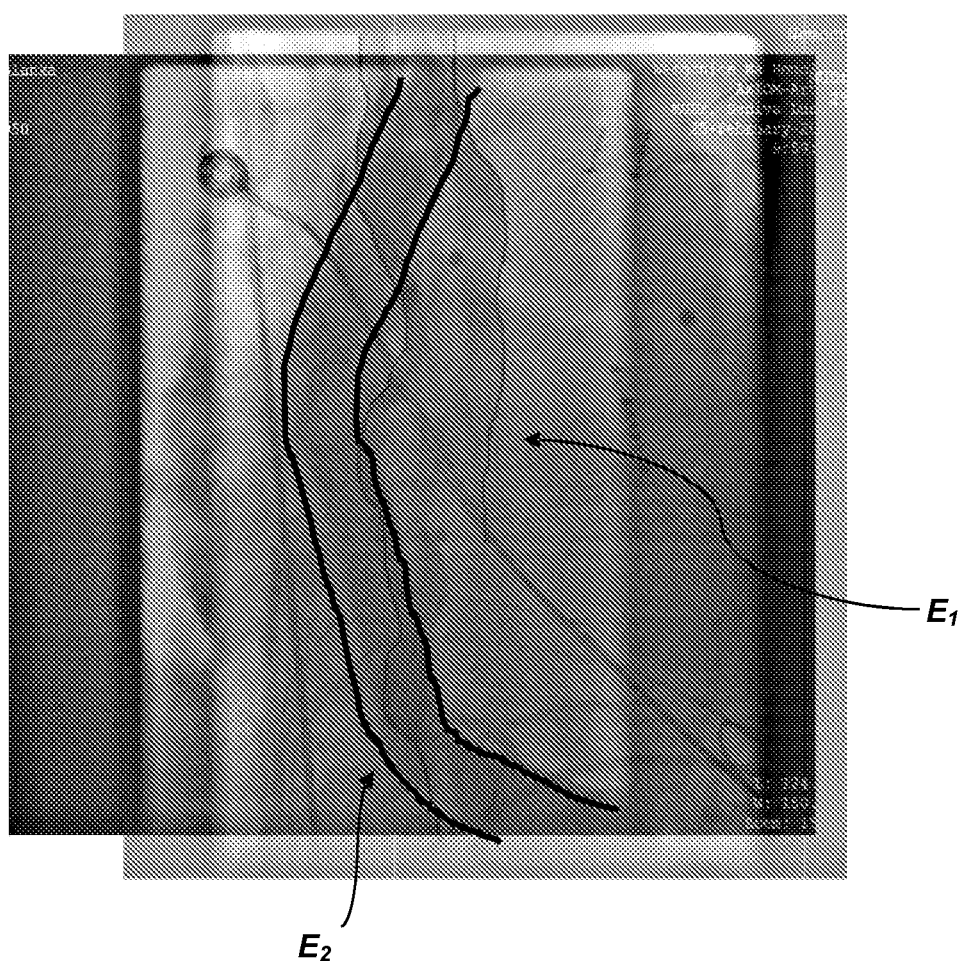

In use, as shown in FIGS. 7 through 9, a positioning device 10 (or any other embodiment of positioning device) according to this disclosure, with its expandable element 30 in an unexpanded state (see, e.g., FIG. 7) may be inserted into a body of a subject and introduced to a desired location within the subject's body (e.g., into a hollow organ; into a long organ, such as an esophagus E, a large intestine, a urethra, etc.; into a cavity; etc.). The particular location and, optionally, the particular orientation of the expandable element 30 within the subject's body may be determined during or after insertion by any suitable technique (e.g., radiography, etc.). If necessary, the position and/or orientation of the expandable element 30 may be adjusted until it is at a desired location and in a desired orientation.

With the expandable element 30 at an appropriate location within the subject's body, the expandable element 30 may be expanded, as shown in FIG. 8, to manipulate the body; for example, the organ within which the expandable element 30 resides or organs that are adjacent to a cavity within which the expandable element 30 resides (e.g., the esophagus E, etc.). The manner in which the expandable element 30 is expanded (e.g., the order in which its sections 32, 34, 36 are expanded, the extent to which the expandable element 30 or one or more of its sections 32, 34, 36 are expanded, etc.) may be controlled. Without limitation, the expandable element 30 may be expanded in a manner that minimizes trauma, in a manner that provides desired movement or reshaping of the organ in which the expandable element 30 resides, etc. In some embodiments, expansion of the expandable element 30 may be visualized (e.g., by radiography, etc.) to confirm that the manner and/or extent of expansion provides one or more desired results (e.g., minimization of trauma, reshaping and/or movement to a desired extent, reshaping and/or movement to a desired extent, etc.). An expandable element 30 and the manner in which it is placed in its expanded state may be configured to move or otherwise manipulate a portion of a long, hollow organ with minimal or no movement of portions of the long, hollow organ that are proximal and distal to the expandable element 30; i.e., without distending the long, hollow organ.

FIG. 9 shows the movement achieved between the orientation of expandable element 30 depicted by FIG. 7 (unexpanded) and the orientation of expandable element 30 depicted by FIG. 8 (expanded). In the embodiment illustrated by FIGS. 7 through 9, the esophagus E (FIGS. 7 and 8) has been moved from a first position $E_1$, in which the esophagus E is adjacent to the left atrium of the heart, to a second position $E_2$, which is about 32 mm away from the first position $E_1$ and which is spaced apart from the left atrium of the heart.

With the expandable element 30 holding the organ in a manipulated state, another procedure may be conducted. As a non-limiting example, an expandable element 30 may deflect an appropriate portion of an esophagus away from the left atrium of the heart during a left atrial ablation procedure. As another non-limiting example, an expandable element 30 may deflect an appropriate portion of a large intestine or a urethra away from a prostate during biopsy or surgical treatment of a prostate.

Once the surgical procedure is complete or manipulation of the organ is no longer needed, the expandable element 30 may be collapsed around the shaft 20 of the positioning device 10. The expandable element 30 and the remainder of the positioning device 10 may then be removed from the subject's body.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A positioning device capable of being introduced against an interior surface of an organ and of diverting a pathway of a portion of the organ, comprising:
    a shaft with a longitudinal axis; and
    an expandable element at a distal end of the shaft, the expandable element being:
        substantially flaccid in an unexpanded state and substantially rigid and substantially non-compliant when in an expanded state; and
        asymmetrical about the longitudinal axis in the expanded state such that the positioning device, in the expanded state, is capable of repositioning the organ,
    the expandable element comprising a balloon expandable to a shape that includes a plurality of bends capable of diverting a portion of the organ, the balloon including:
    a diverting element that extends away from the longitudinal axis at a first bend defining a first obtuse angle when the expandable element is in the expanded state;
    a spacing element distal to, continuous with, and extending away from the diverting element at a second bend defining a second obtuse angle to the diverting element when the expandable element is in the expanded state, at least a portion of a length of the spacing element being oriented substantially parallel to the longitudinal axis when the expandable element is in the expanded state; and
    a convergent element distal to, continuous with, and extending away from the spacing element at a third bend defining a third obtuse angle to the spacing element when the expandable element is in the expanded state, the convergent element extending toward the longitudinal axis when the expandable element is in the expanded state,
    with corners at the first bend, at the second bend between the diverting element and the spacing element, and at the third bend between the spacing element and the convergent element respectively defining the first obtuse angle between the longitudinal axis and the diverting element, the second obtuse angle between the diverting element and the spacing element, and the third obtuse angle between the spacing element and the convergent element,
    the diverting element, the spacing element, and the convergent element having cross-sectional shapes and cross-sectional dimensions capable of diverting the organ upon expansion of the expandable element without distending the organ or causing trauma to the organ upon expansion of the expandable element,
    the cross-sectional shapes and cross-sectional dimensions of the diverting element, the spacing element, and the convergent element being the same as one another and uniform along lengths of the diverting element, the spacing element, and the convergent element when the expandable element is expanded.

2. The positioning device of claim 1, wherein the shaft includes a lumen for communicating an inflating medium into a cavity of the expandable element to transition the expandable element from the unexpanded state to the expanded state.

3. The positioning device of claim 1, further comprising:
    a positioning control associated with the shaft, the positioning control capable of changing at least one of a position, an orientation and a shape of the expandable element.

4. The positioning device of claim 3, wherein the positioning control comprises a wire.

5. The positioning device of claim 1, wherein the expandable element includes a plurality of chambers.

6. The positioning device of claim 5, wherein the plurality of chambers includes:
    a first chamber at a proximal end of the expandable element; and
    a second chamber at a distal end of the expandable element, the first chamber separately inflatable from the second chamber.

7. The positioning device of claim 1, wherein the expandable element is formed from a substantially non-compliant material.

8. A positioning device capable of being introduced against an interior surface of a hollow organ and of diverting a pathway of a portion of the hollow organ, comprising:
    a shaft with a longitudinal axis;
    an expandable element at a distal end of the shaft, the expandable element including:
        a diverting element that, when inflated, forms a first bend defining a first obtuse angle to the longitudinal axis that causes the diverting element to extend away from the longitudinal axis;

a spacing element distal to the diverting element that, when inflated, forms a second bend defining a second obtuse angle with the diverting element, with at least a portion of a length of the spacing element being oriented substantially parallel to the longitudinal axis; and a convergent element distal to the spacing element that, when inflated, forms a third bend defining a third obtuse angle with the spacing element and causes the convergent element to extend toward the longitudinal axis, with a first corner defined at the first bend, a second corner defined at the second bend, and a third corner defined at the third bend, cross-sectional shapes and cross-sectional dimensions of the diverting element, the spacing element, and the convergent element being substantially the same as one another and substantially consistent along lengths of the diverting element, the spacing element, and the convergent element when the diverting element, the spacing element, and the convergent element are inflated, the cross-sectional shapes and cross-sectional dimensions capable of diverting a portion of the hollow organ without distending the hollow organ or causing trauma to the hollow organ upon inflation of the expandable element.

9. The positioning device of claim 8, wherein the expandable element comprises an inflatable balloon having a deflated state and an inflated state.

10. The positioning device of claim 9, wherein the expandable element is flaccid in the deflated state and substantially rigid in the inflated state.

11. The positioning device of claim 8, wherein the expandable element includes at least two separately inflatable chambers.

12. A method for moving a portion of an esophagus away from a left atrium of a heart, comprising:

inserting a shaped, non-compliant expandable element into the esophagus, the shaped, non-compliant expandable element positioned and oriented to deflect a portion of the esophagus away from the left atrium of the heart;

inflating the shaped, non-compliant expandable element to provide a rigid deflecting element with a plurality of continuous, angularly oriented sections having constant cross-sectional shapes and dimensions with corners therebetween to impart the shaped, non-compliant expandable element with a series of bends capable of deflecting the portion of the esophagus away from the left atrium of the heart without distending the esophagus or causing trauma to the esophagus.

13. The method of claim 12, further comprising:
conducting a procedure on the left atrium of the heart with the portion of the esophagus deflected away from the left atrium of the heart.

14. The method of claim 12, further comprising:
changing at least one of a position, an orientation and a shape of the shaped, non-compliant expandable element within the portion of the esophagus.

15. The method of claim 12, further comprising:
collapsing the shaped, non-compliant expandable element; and
removing the shaped, non-compliant expandable element from the esophagus.

* * * * *